(12) United States Patent
Krespi et al.

(10) Patent No.: US 11,419,998 B2
(45) Date of Patent: Aug. 23, 2022

(54) DEVICE FOR SECURING AIRWAY AND VENTILATION DURING ROBOTIC SURGERY OF THE HEAD AND NECK

(71) Applicant: Valam Corporation, New York, NY (US)

(72) Inventors: Yosef Krespi, New York, NY (US); Robert Koorn, Redding, CT (US)

(*) Notice: Subject to any disclaimer, the term of this patent is extended or adjusted under 35 U.S.C. 154(b) by 0 days.

(21) Appl. No.: 16/022,683

(22) Filed: Jun. 28, 2018

(65) Prior Publication Data

US 2019/0030271 A1 Jan. 31, 2019

Related U.S. Application Data

(60) Provisional application No. 62/528,028, filed on Jun. 30, 2017.

(51) Int. Cl.
*A61M 16/06* (2006.01)
*A61M 16/08* (2006.01)
(Continued)

(52) U.S. Cl.
CPC .... *A61M 16/0605* (2014.02); *A61M 16/0409* (2014.02); *A61M 16/0488* (2013.01); *A61M 16/0683* (2013.01); *A61M 16/0816* (2013.01); *A61B 90/30* (2016.02); *A61B 90/361* (2016.02); *A61M 2034/301* (2016.02); *A61M 16/01* (2013.01); *A61M 16/021* (2017.08); *A61M 16/0425* (2014.02); *A61M 16/0434* (2013.01);
(Continued)

(58) Field of Classification Search
CPC ............. A61M 16/04; A61M 16/0409; A61M 16/0463; A61M 16/0486; A61M 16/0465; A61M 16/0488; A61M 16/0816; A61M 16/0425; A61M 16/0434; A61B 2034/301; A61B 2034/302; A61B 2034/303; A61B 34/32; A61B 34/35; A61B 34/37; A61B 90/361; A61B 90/36; A61B 90/30; A61B 17/00234
See application file for complete search history.

(56) References Cited

U.S. PATENT DOCUMENTS

| | | | | |
|---|---|---|---|---|
| 5,040,532 A | * | 8/1991 | Alfery | A61M 16/0486 128/207.15 |
| 5,551,946 A | * | 9/1996 | Bullard | A61B 1/2676 600/194 |

(Continued)

OTHER PUBLICATIONS

Nabil Simaan, Russell Taylor, Paul Flint, "High Dexterity Snake-Like Robotic Slaves for Minimally Invasive Telesurgery of the Upper Airway", 2004, Springer-Verlag Berlin Heidelberg, pp. 17-24 (Year: 2004).*

*Primary Examiner* — Joseph D. Boecker
*Assistant Examiner* — Brian T Khong
(74) *Attorney, Agent, or Firm* — Joseph P. Aiena

(57) ABSTRACT

There is provided an LMA mask integrated for robotic surgery with ventilation or anesthesia tubes and for receiving the robot head with medical instruments through the mask. The inflatable cuff of the mask surrounds the robot head and ventilation so that the items necessary for surgical procedures are contained within a compact defined area. Increased maneuverability and visibility for the medical professional. Integration of the mask with processes for ventilation or anesthesia by accessories is also provided.

8 Claims, 16 Drawing Sheets

(51) Int. Cl.
*A61M 16/04* (2006.01)
*A61M 16/01* (2006.01)
*A61B 34/30* (2016.01)
*A61M 16/00* (2006.01)
*A61B 90/00* (2016.01)
*A61B 90/30* (2016.01)

(52) U.S. Cl.
CPC ... *A61M 16/0493* (2014.02); *A61M 2205/587* (2013.01)

(56) References Cited

U.S. PATENT DOCUMENTS

| | | | |
|---|---|---|---|
| 8,998,798 B2 * | 4/2015 | Hayman | A61B 1/00082 600/120 |
| 9,138,129 B2 * | 9/2015 | Diolaiti | A61B 1/00163 |
| 2008/0027464 A1 * | 1/2008 | Moll | A61B 1/307 606/130 |
| 2010/0274087 A1 * | 10/2010 | Diolaiti | A61B 34/37 600/118 |
| 2011/0071508 A1 * | 3/2011 | Duval | A61B 1/00087 606/1 |
| 2013/0096379 A1 * | 4/2013 | Goldberg | A61M 16/04 600/109 |
| 2013/0096572 A1 * | 4/2013 | Donhowe | A61B 34/10 606/130 |
| 2014/0096766 A1 * | 4/2014 | Avitsian | A61B 1/00135 128/200.26 |
| 2014/0150782 A1 * | 6/2014 | Vazales | A61M 16/0463 128/202.16 |
| 2014/0309494 A1 * | 10/2014 | Molnar | A61B 7/003 600/109 |
| 2014/0323806 A1 * | 10/2014 | Brain | A61B 1/2733 600/115 |
| 2015/0031951 A1 * | 1/2015 | Furlong | A61B 1/00094 600/106 |
| 2015/0099934 A1 * | 4/2015 | Sartore | A61B 1/00091 600/187 |
| 2015/0119900 A1 * | 4/2015 | Simaan | A61B 1/00006 606/130 |
| 2016/0001038 A1 * | 1/2016 | Romo | A61M 25/005 604/526 |
| 2016/0114117 A1 * | 4/2016 | Cook | A61B 1/005 600/109 |
| 2016/0235486 A1 * | 8/2016 | Larkin | B25J 9/1671 |
| 2017/0231572 A1 * | 8/2017 | Lowery | A61B 5/6857 600/301 |

* cited by examiner

DEVICE FOR SECURING AIRWAY AND VENTILATION DURING ROBOTIC SURGERY OF THE HEAD AND NECK

CROSS REFERENCE TO RELATED APPLICATIONS

This application claims the benefit of and priority to U.S. Provisional Application Ser. No. 62/528,028 filed on Jun. 30, 2017, incorporated by reference in its entirety herein.

FIELD OF THE INVENTION

The present invention relates to a device for use in surgery of the head and neck, and more particularly to a device for use with robotic surgery to provide ventilation and secure a patient's airway.

BACKGROUND

While there have recently been advances in robotic surgery, there are still various limitations, including in the area of surgery of the head and neck. One of these limitations is the obstruction of the surgeon's view during the surgery by various tubes and equipment. Removal of the tubes, such as those for ventilation or anesthesia, is possible to assist with the surgeon's view, however this creates the readily apparent drawback to the patient's ventilation or of providing only limited anesthesia for a period of time.

SUMMARY

The present invention provides a device and processes of using the device to overcome the above noted issues. The device of the present invention is for an integrated laryngeal mask airway (LMA) which includes at least one anesthesia/ventilation line along with the robot head for surgical procedures which is incorporated through the airway tube. The robot head and anesthesia or ventilation line extend out from the airway tube opening through one or more channels and into the mouth opening of the cuff piece of the LMA. More particularly, there is included a mask for use in robotic surgery including an airway tube connected to a cuff piece with the cuff piece having an inflatable cuff integrally formed with a back section to the cuff piece. The inflatable cuff has an inner edge which defines a mouth of the inflatable cuff and an inflation line extending from the inflatable cuff. The back section includes a first channel for receiving a robot head with at least one medical instrument and a second channel for receiving a ventilation tube. The robot head and the ventilation tube are capable of extending from the mouth of the cuff for medical procedures by controlling a robot connected to the robotic head. A camera and light are on the robot head for visibility. In an embodiment, the cuff of the mask has a third channel for receiving an anesthesia tube as well.

The present invention allows for airway access at all times without removing the robot head out during the surgical process. The procedure starts and ends with usual oral or nasal intubation, however, with the present invention there is the ability to conduct laryngeal and pharyngeal surgery without an endotracheal tube in place. The present invention also provides improved access and visualization of the surgical site.

A laryngeal mask airway (LMA) type mask is used for ventilation, around the robotic head and instruments. The present invention uses the LMA cuff to seal structures around the larynx and be able to assist with ventilation. The use of a protective, condom like sleeve to wrap the proximal part of the robot head is present to secure the LMA cuff. In an embodiment, the present invention uses a rubber diaphragm like membrane to seal the robot head. In an embodiment, one of the robotic instrument channels which comes through the masks with the surgical device is used for the anesthesia access and delivery to the patient.

The present invention allows that during the robotic phase of a medical procedure, there is no endotracheal tube in place. There are also provided processes for delivering anesthesia or ventilation during robotic surgery with the present invention by use of different accessories, such as adaptors or tube exchangers.

BRIEF DESCRIPTION OF THE DRAWINGS

The accompanying drawings illustrate various embodiments of the present invention and system and are part of the specification. The illustrated embodiments are merely examples of the present system and invention and do not limit the scope thereof.

DETAILED DESCRIPTION

Figure 1:
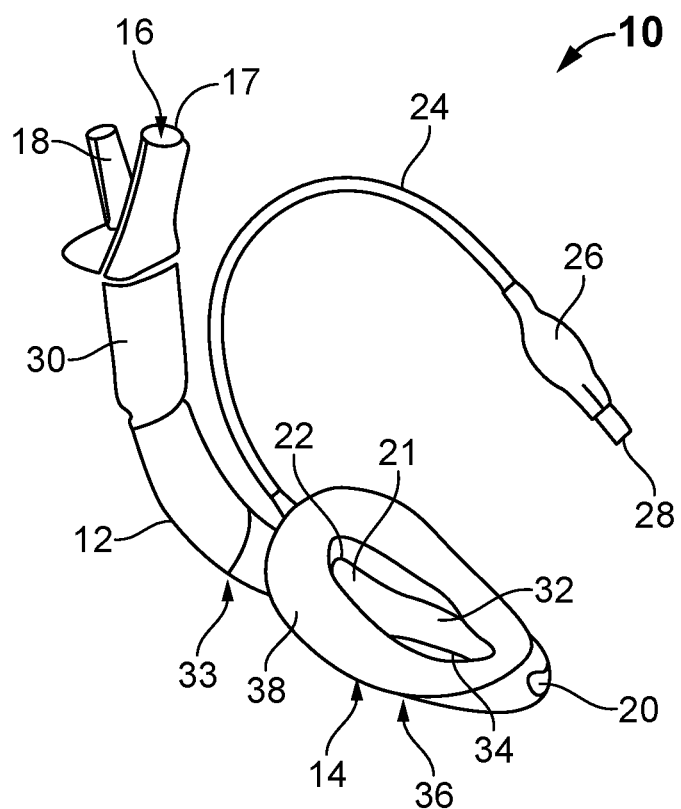
FIG. 1 is an illustration of a laryngeal mask airway (LMA) device with tubes indicated.

Referring to FIG. 1, there is illustrated a standard LMA mask 10 which includes an elongated and flexible airway tube 12 having an airway tube opening 16 at a first end 17 and an airway tube orifice 22 at a second end 21 of the airway tube 12. The first end 17 of the airway tube 16 also includes a drain tube 18 connected to or inserted into the airway tube 12. An integral bite block 30 may also be positioned over the airway tube 12 to prevent collapse of the airway tube 12 from external pressure, such as biting by the patient. The second end 21 of the airway tube is connected to the inflatable cuff piece 14, which has an integrally formed stem section 33 for receiving the second end 21 of the airway tube 12. The stem section 33 extends into a larger head area 36 which opens into an elongated opening 34 or mouth, which may be oval shaped. The head area provides protection against epiglottic obstruction 32. Surrounding the head area 36 and integrally connected therewith is an inflatable cuff 38, which receives and inflation line 24 that is connected to a pilot balloon 26 and valve 28. The inflatable cuff 38 can be inflated by forcing air through valve 28, such as by inserting a syringe into the valve 28 and depressing the syringe plunger. Likewise, the inflatable cuff 38 can be deflated by drawing the syringe plunger back. Head area 36 may include a drain tube orifice 20.

Figure 2:
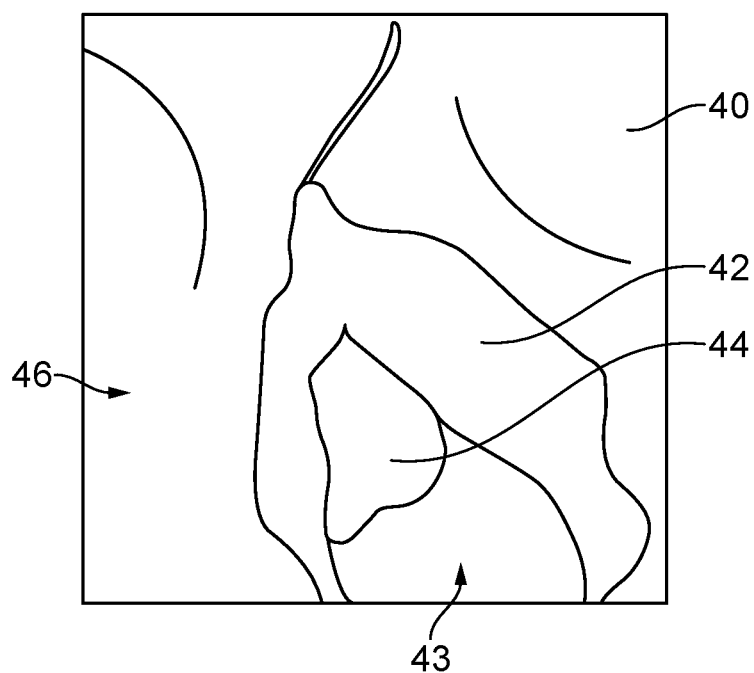
FIG. 2 is an illustration of a vocal cord polyp obstructing a patient's airway.

FIG. 2 is a patient 40 who suffers from an obstruction on their airway 43, such as a polyp 44 on the vocal cord 42. The present invention is used in surgical procedures for removal of such obstructions 44. As indicated in FIG. 2, at the surgical site, the area 46 inside and surrounding the patient's 40 airway 43 for performing any surgery is narrow and limited. This area 46 is further reduced upon introduction of instruments and ventilation tubes, thereby reducing visibility and maneuverability to the surgeon as well. The present invention maximizes the area 46 available during robotic surgery for the surgeon's visibility and maneuverability without sacrificing ventilation or anesthetic procedures. As set out herein, this is accomplished having airway access at all times without removing the robot head out during the surgical procedure. Further, the present invention allows a surgeon to conduct laryngeal and pharyngeal surgery without the endotracheal tube in place.

Figure 3:
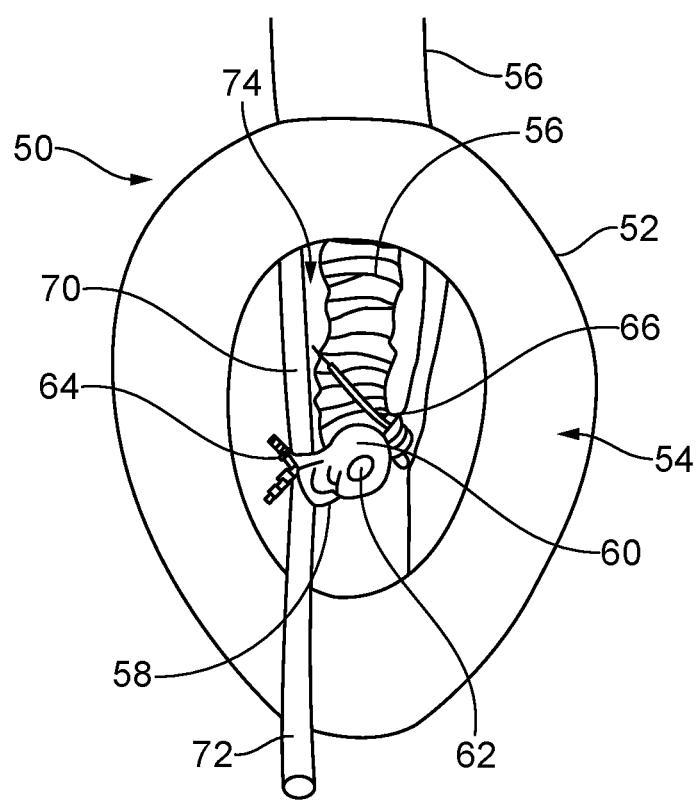
FIG. 3 is a schematic illustration of the LMA of the present invention with the robot head and ventilation integrated in the LMA.

Referring now to FIG. 3, there is shown the integrated LMA of the present invention 50. The device of the present invention 50 is an integrated LMA with the robot head 58 and ventilation included in the LMA. The present invention 50 includes the cuff piece 52 of an LMA with an inflatable cuff 54. With the present invention 50, the robot 56 and ventilation line 70 are received through the back 74 of the cuff piece 52, by two separate channels, although a single wider channel to accommodate both is within the scope of the present invention. This allows the LMA of the present invention 50 to provide the robot head 58 with surgical instruments and ventilation into the surgical area in a contained, integrated single device of the LMA of the present invention. This is illustrated in FIG. 3, which shows that at the end of the robot head 53 is a light 60 and camera 62 to assist the medical professional with visibility of the surgical procedure. Instruments 64 and 66 for various medical procedures are included at end of robot head 58 as well. During this time, the patient is still ventilated by tube as well through the mask. This provides greater access and visualization of the surgical site and area by integrating the robot head and ventilation tubes to within the area occupied by the LMA.

Figure 4:
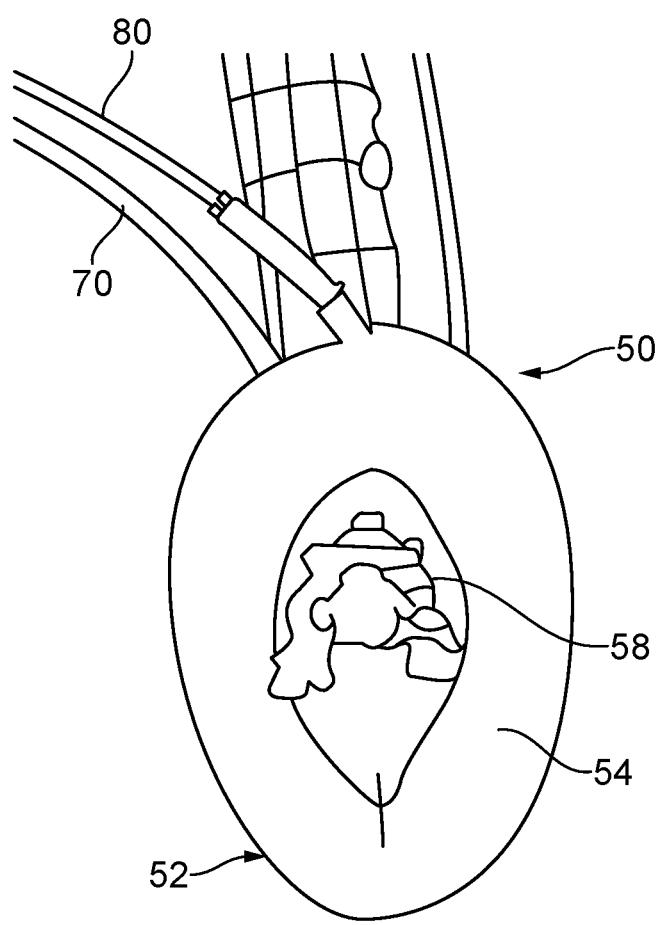
FIG. 4 is a front view of the LMA of the present invention.
Figure 5:
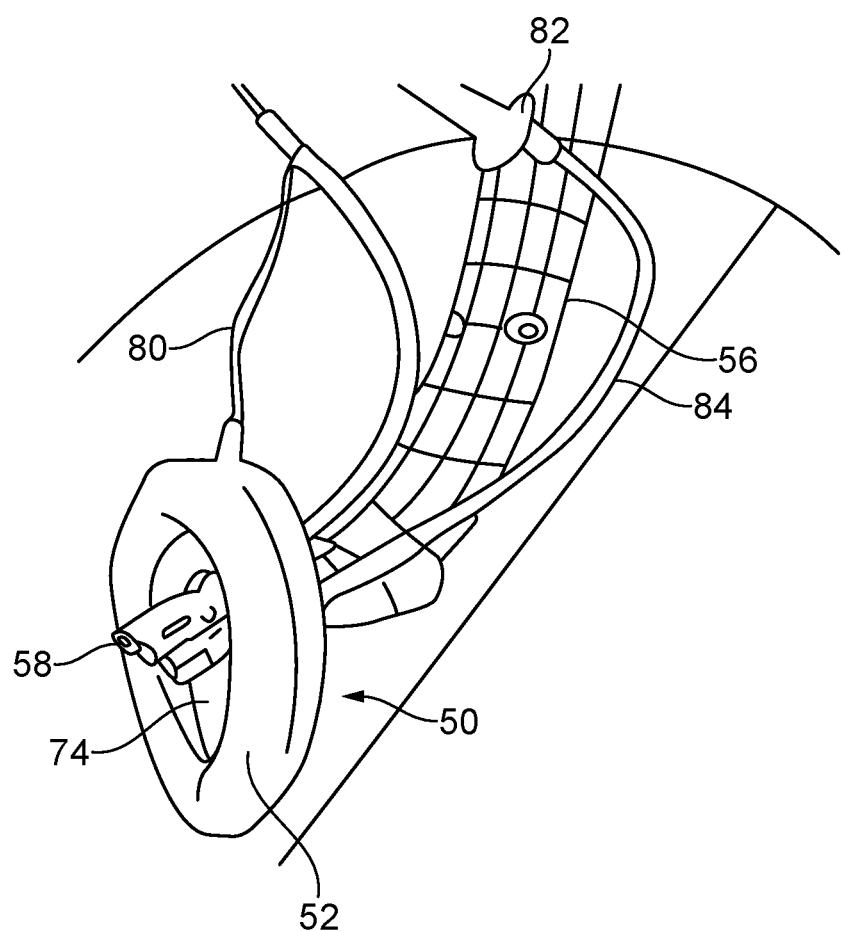
FIG. 5 is a side view of the present invention including an anesthesia tube.

FIGS. 4 and 5 show front and side views respectively of the present invention 50. The robot head 58 is shown again descending from the robot arm and protruding through the back 74 of mask cuff piece 52 and contained within the area created by and surrounded by the inflatable cuff 54. Flexible tubes 70 and 84 are included and positioned on respective sides of the robot head 58. An instrument for surgery may be included here as indicated in FIG. 3. The tubes 70 and 84 may be used for ventilation and/or anesthesia. Further, accessories can be included and attached with the tubes, such as shown for tube 84 in FIG. 5 which may connect to an adaptor 82 for ventilation or anesthesia. An adaptor, such as those under the brand name Portex are suitable for use in the present invention. The present invention 50 also includes an inflation line 80 extending from the inflatable cuff 54 and connected with a syringe for maintaining an adjustable and desirable size to the cuff so that a proper fit with the patient's surrounding tissue may be achieved. Two side by side channels are included in the present invention for the robot and the instruments, but it should be noted that a third channel can also be included for ventilation in other embodiments.

Further, the airway tube for use with the present invention is smaller, such as size 6 or 7 as known in the art, to accommodate the robot head 58. It should be noted that the bite block and drain tube of the prior LMA designs are not necessary. Overall, this design of the present invention allows the surgeon to perform laryngeal surgery without the presence of an endotracheal tube and therefore, the surgeon's view is no longer obstructed by the endotracheal tube during surgery.

Figure 6:
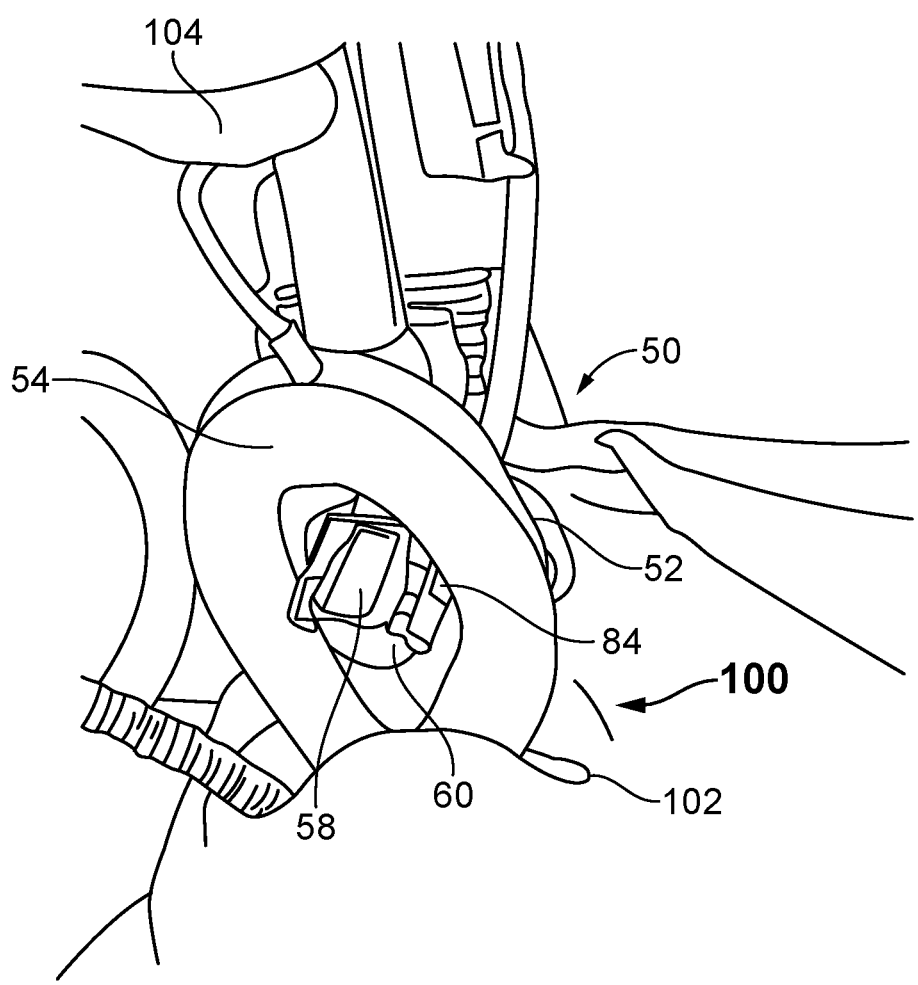
FIG. 6 is a view of the present invention as inserted into a patient's mouth for surgery.

FIG. 6 demonstrates the present invention 50 integrated LMA as it is inserted into the mouth 102 of a patient 100 for a surgical procedure by medical professional 104. The robot head 58 with flexible tubes 70 and 84 is contained within the mask 50 and surrounded by the inflatable cuff 54, which is partially deflated for insertion into the mouth 102 of the patient 100. The light 60 on the robotic head 58 is activated in this illustration. As part of the present invention LMA 50, there are various means to seal the integrated LMA to create an air tight seal with the patient's tissue in the surgical area where the mask is placed. In order to seal the back of the mask where the robotic head enters the mask, a diaphragm can be used which is pliable and thereby hugs the robotic head 58. Alternatively, a condom-like cover may be used, which rolls back and hugs the robot head 58 to maintain the hermetic seal of the mask.

Figure 7:
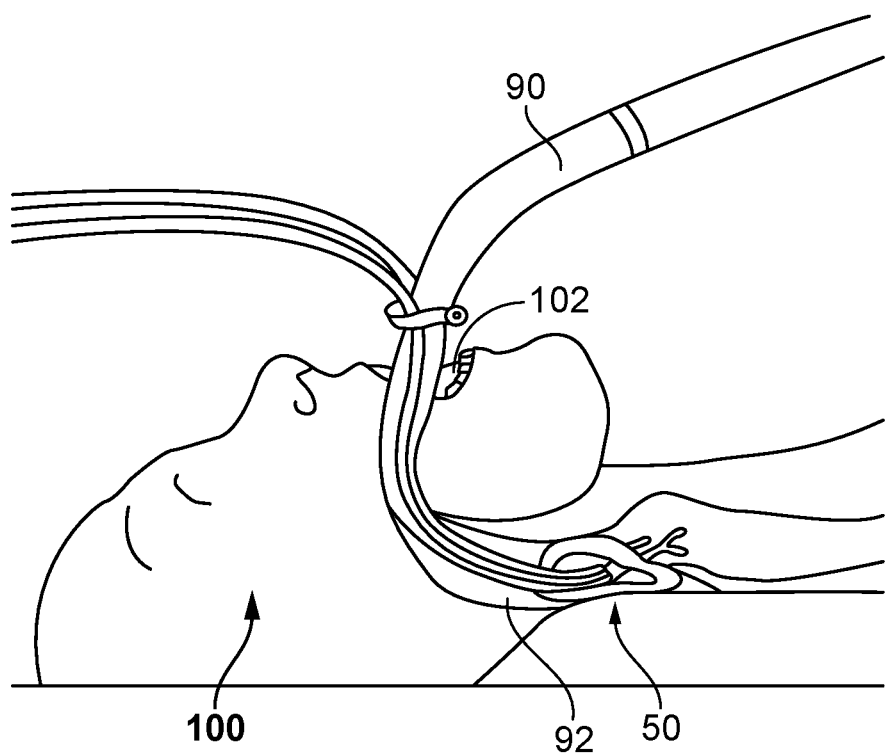
FIG. 7 is an illustration of the present invention LMA in use with a patient during robotic surgery from a cross sectional view.

With reference to FIG. 7, there is a schematic that illustrates robotic surgery with robotic arm 90. The LMA of the present invention 50 in use on a patient 100 with insertion of the LMA 50 into the patient's mouth 102 and down into throat area 92. Inside the patient's throat, the cuff 54 of the LMA 50 is inflated to seal the patient's airway for the surgical procedure and allow ventilation to continue. The robotic head 58 is also extended into the patient's mouth 102 and throat so that the surgical procedure on the patient can be performed.

Figure 8:
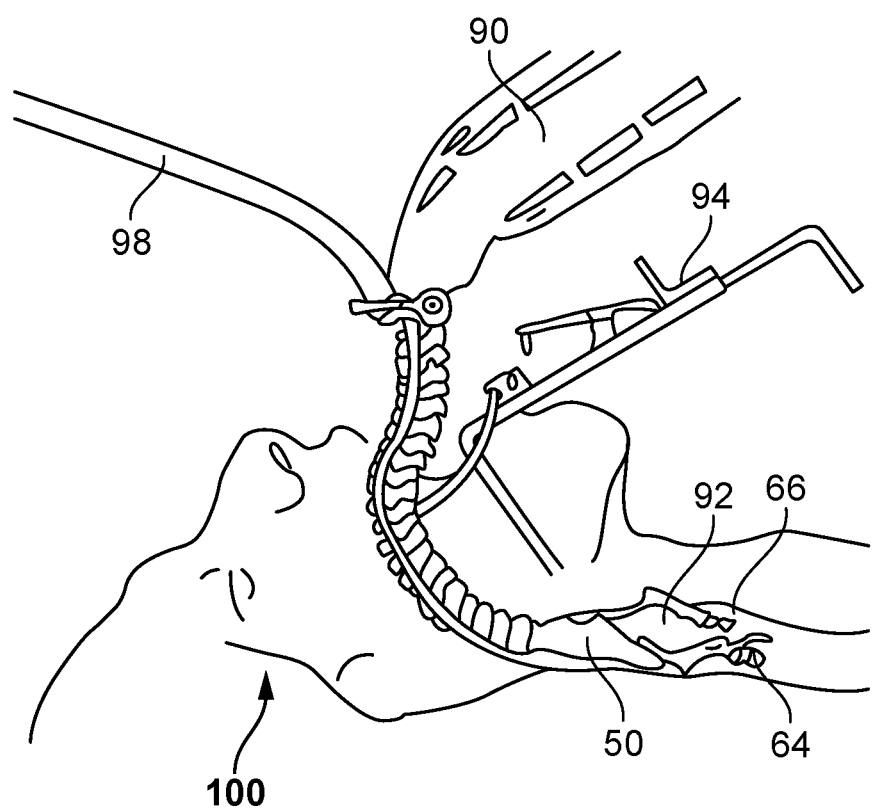
FIG. 8 is an illustration of the present invention LMA and robot along with a retractor and flexible instruments in use with a patient from a cross section.

In FIG. 8, there is shown a patient 100 with the present invention 50 inserted into throat area 92 for robotic surgery. As the medical procedure is performed, a retractor 94 may also be used as normal in the art to open the patient's mouth and maintain the mouth in a fixed open position. As the integrated LMA of the present invention includes the robot head and ventilation within the area occupied by the mask 50 in the throat 92, there is greater maneuverability for the surgeon. The flexible surgical instruments 64 and 66 are shown protruding from the integrated mask 50. These instruments and the robot head are controlled by the medical professional operating the mechanical arm 98 and robot 90.

Figure 9:
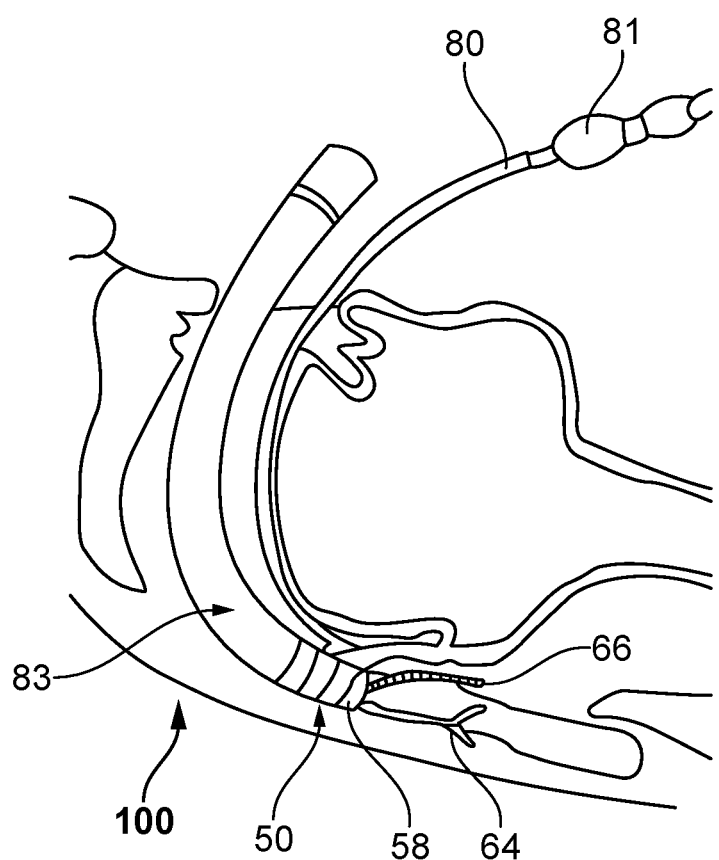
FIG. 9 is another illustration of the present invention LMA and robot in use on a patient, with the robot head shown.

FIG. 9 illustrates a cross section of a patient with the integrated LMA of the present invention 50 positioned in the throat area of the patient 100. An airway tube 83 extends from outside the patient's mouth down into the throat area where the LMA has been positioned. The inflation line 80 connects to the LMA so that the medical professional may inflate or deflate the cuff of the LMA as necessary through the use of the valve 81 that is connected to a standard syringe. The head 58 of the robot 56 is shown with instruments 64 and 66 extending from the robot head 58.

Figure 10A:
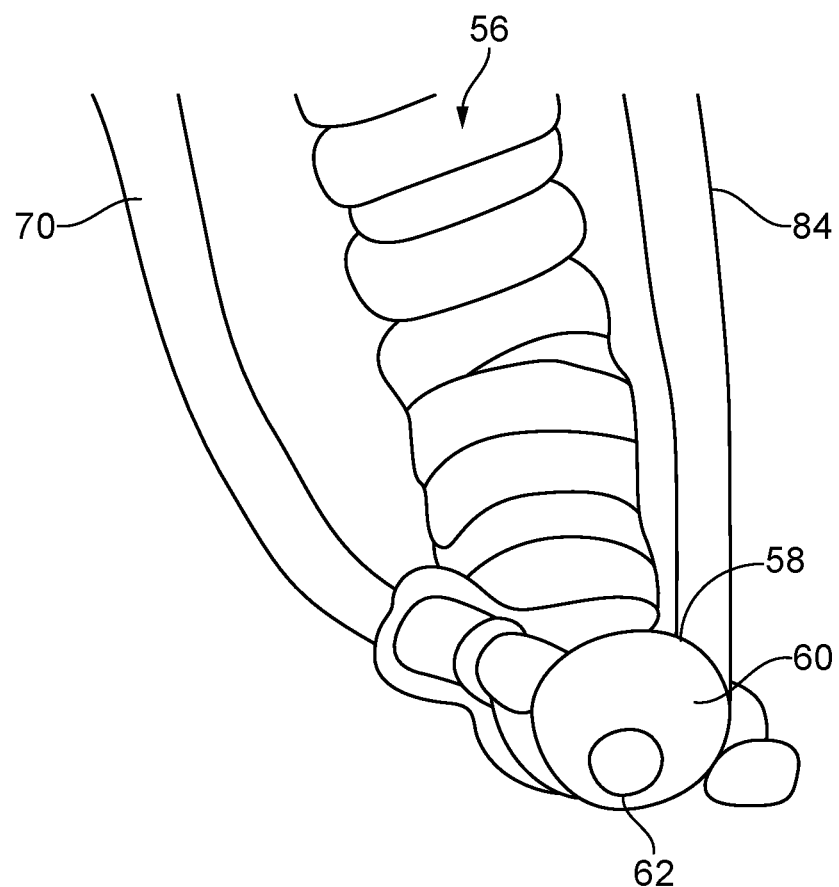
FIG. 10A shows the front end of the flexible robotic device with camera light on for illumination.
Figure 10B:
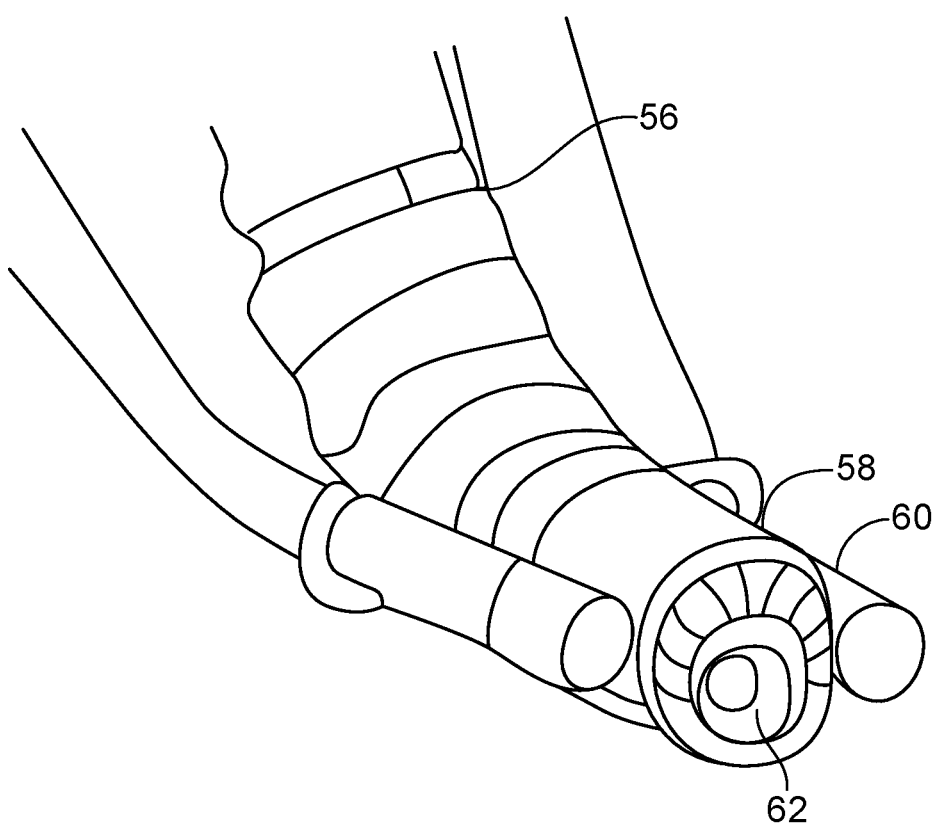
FIG. 10B shows the front end of the flexible robotic device with the camera and light turned off.

Referring now to FIG. 10A, there is shown a front end of the flexible robotic device 56 with camera 62 and light 60 turned on at the robot head 58. Flexible tubes 70 and 84 are attached to the sides of the robot head 58. Respectively, FIG. 10B shows the robot head 58 of the flexible robotic device 56 with the light 60 and camera 62 turned off.

Figure 11:
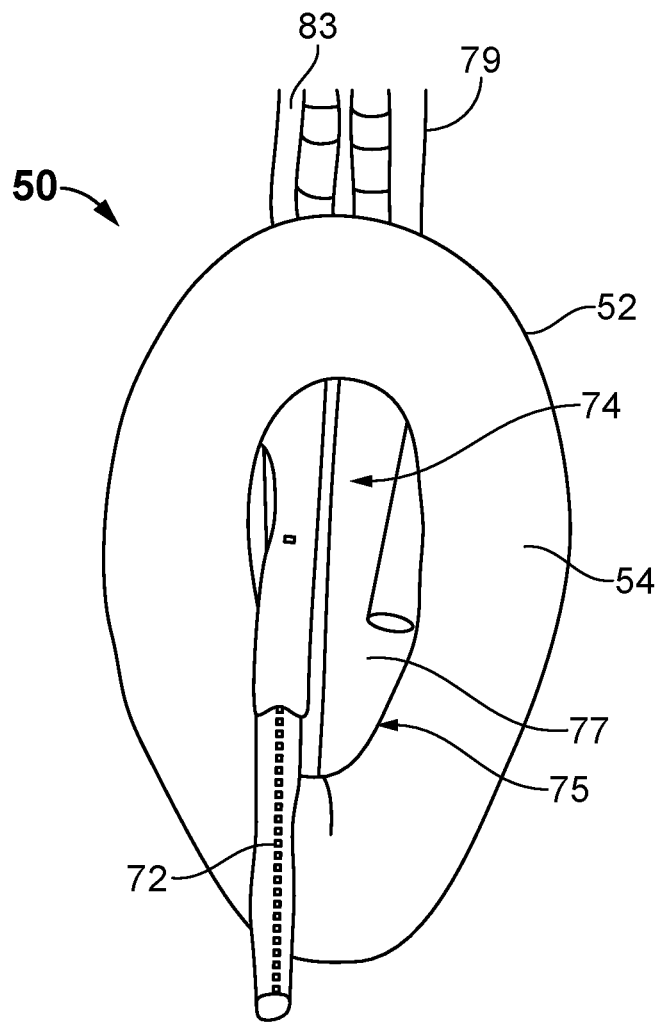
FIG. 11 another front view of the present invention.

FIG. 11 is a front view of the LMA as if it was facing the airway of a patient. There is shown with the LMA of the present invention 50, the airway tube 83 connecting with the cuff piece 52 which has inflatable cuff section 54 as described above. It is this inflatable cuff which seals structures around the larynx when the LMA is in place for surgery. The cuff piece 52 has a back section 74, through which the airway channel enters, and the inflatable cuff 54 connected with the back section. The cuff 54 has an inner edge 75 which forms a mouth or opening 77 inside the cuff 52. Extending through the airway tube channel and into the LMA cuff piece is a ventilation line 72. This line 72 extends through the opening 77 of the cuff and then may be positioned over and beyond the cuff 54. In this manner, the ventilation line may provide ventilation to a patient when the LMA is inserted into a patient's throat for surgery. As seen with FIGS. 3, 4 and 5, in making use of the defined space of the mouth 77 of the LMA, the present invention positions the robotic head (with attached surgical instruments) in this contained location by way of a second channel through the back section 74 of the cuff piece 52. Also seen in FIG. 11 is a pliable diaphragm or condom like piece 79 which can be rolled back, surround, hug, and seal the robot and airway tube 83 with the mask.

Figure 12:
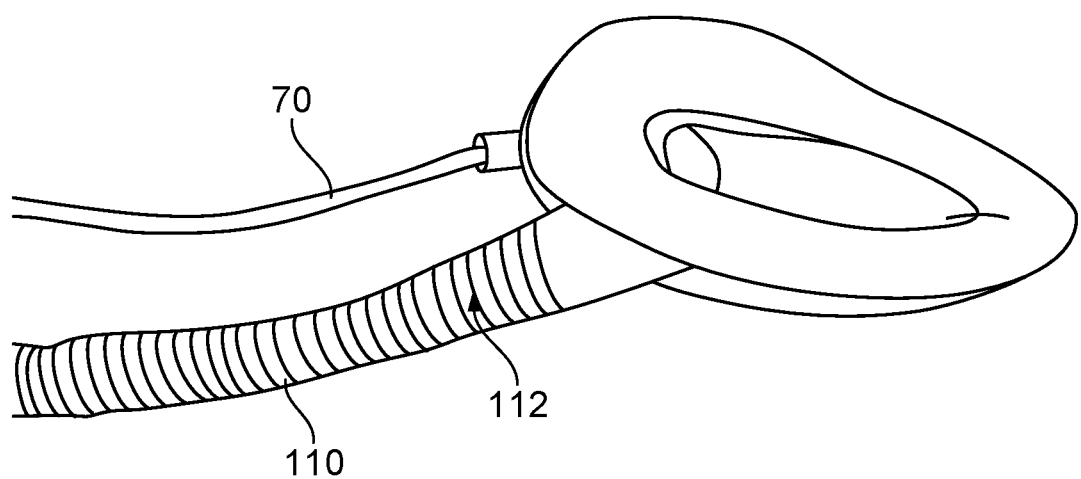
FIG. 12 is an LMA of the present invention in use with a reinforced airway tube.

FIG. 12 illustrates the use of an airway tube which is suitable for use with the present invention and for robotic surgery. This tube is reinforced 110, such as with wires 112 on the inside, and is a smaller radius tube than those used with prior LMAs. This combination makes the tube suited for robotic anesthesia.

Figure 13A:
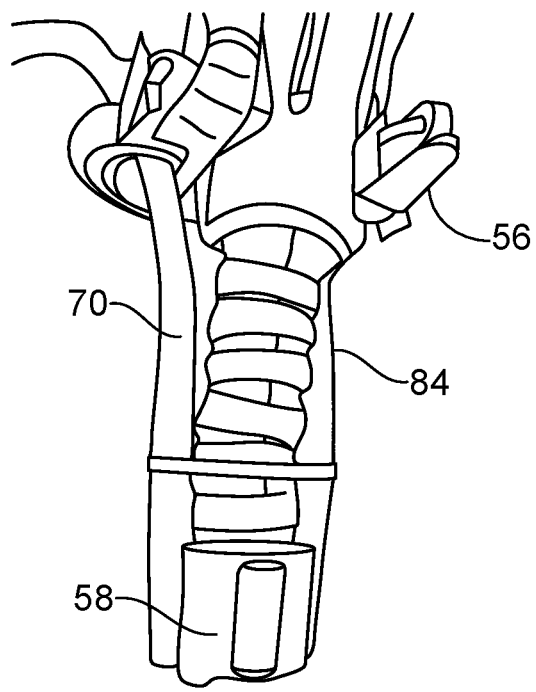
FIGS. 13A and B illustrate the flexible and rigid portions of the robot head.
Figure 13B:
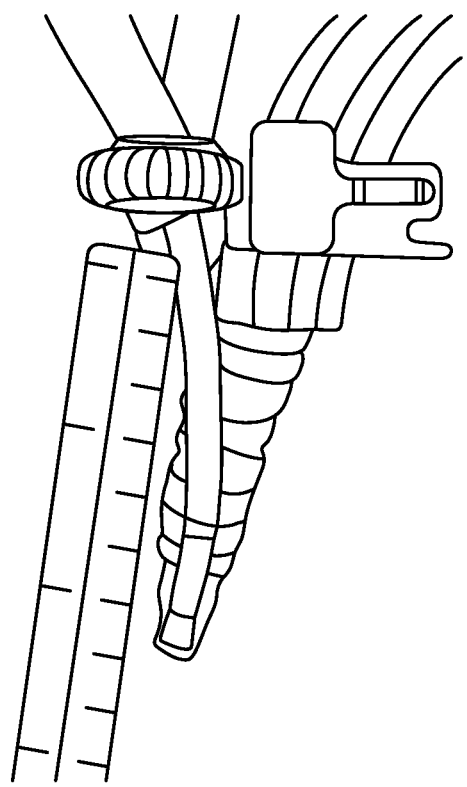

FIGS. 13A and B indicate the flexible and rigid parts of the robot head 58. The flexible instrument channel 70 and 84 are shown positioned on opposite sides of the robot head 58. The robot 56 is shown as well with its rigid structure above. FIG. 13B provides a non-limiting dimension of approximately 6 cm for the distance of the instrument channel 70 from the robot 56 to the robot head 58 at an initial position.

Figure 14A:
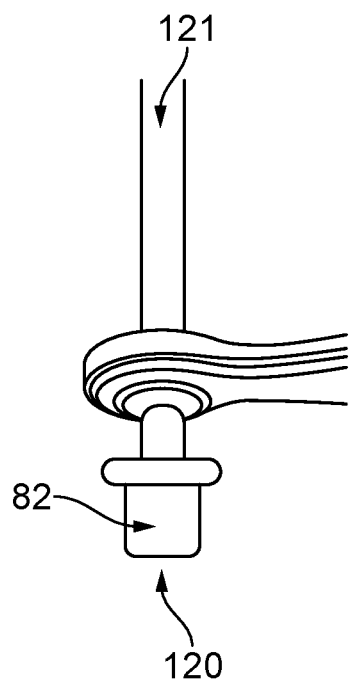
FIGS. 14A and B show the adaptor attached to the robotic instrument channel for ventilation.
Figure 14B:
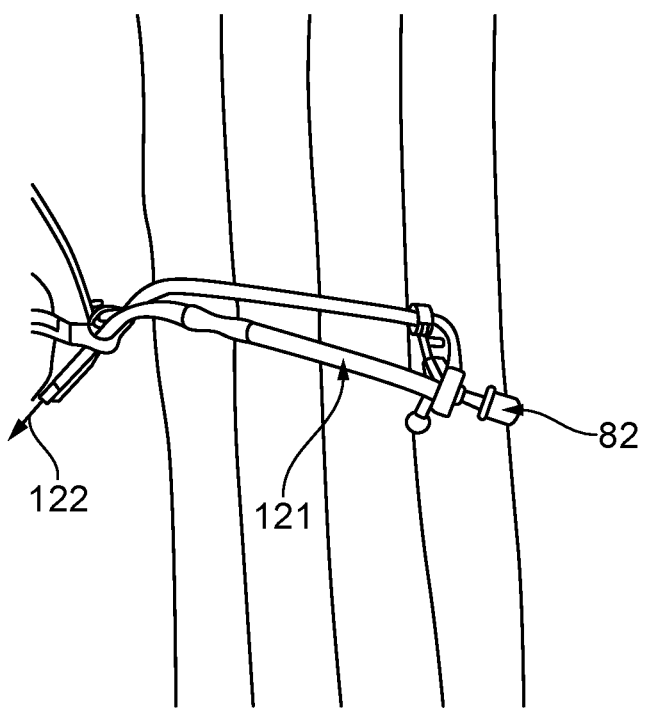

With reference to FIGS. 14A and B, there is shown a process and uses of an adaptor 82 for ventilation in connection with robot surgery and with uses for the present invention. The adaptor 82 may be commercially available adaptors suitable for ventilation or anesthesia, such as those under the brand Portex® by Smiths Medical ASD, Inc. of Minneapolis, Minn. Tubes of size No. 3.5 or smaller are suitable for use in the invention. In FIG. 14A, a Portex® adaptor 82 is shown attached to the robotic instrument channel 121. Flow of ventilation air or anesthesia is indicated by arrow 120 into the adaptor piece 82. Similarly, in the second diagram, FIG. 14B, the adaptor 82 is shown attached to the robotic instrument channel 121 with the medical professional standing behind for reference. At the opposite end of the instrument channel 121, the ventilation or anesthesia flows out of the instrument channel 121, as indicated by flow arrow 122. This is the ventilation or anesthesia flow which will reach the patient as the robotic instrument channel 121 is attached to the robot head 58 and included in the integrated LMA 58 of the present invention. In this manner, instrument channels may be used for jet ventilation or anesthesia during robotic surgery, allowing for a puff of air to reach the patient's lungs as necessary. This assists in optimizing ventilation or anesthesia for the patient during surgery. For each of the embodiments described in FIGS. 1 through 15, the anesthesia amounts, types and dosage are as known to those in the art.

Figure 15:
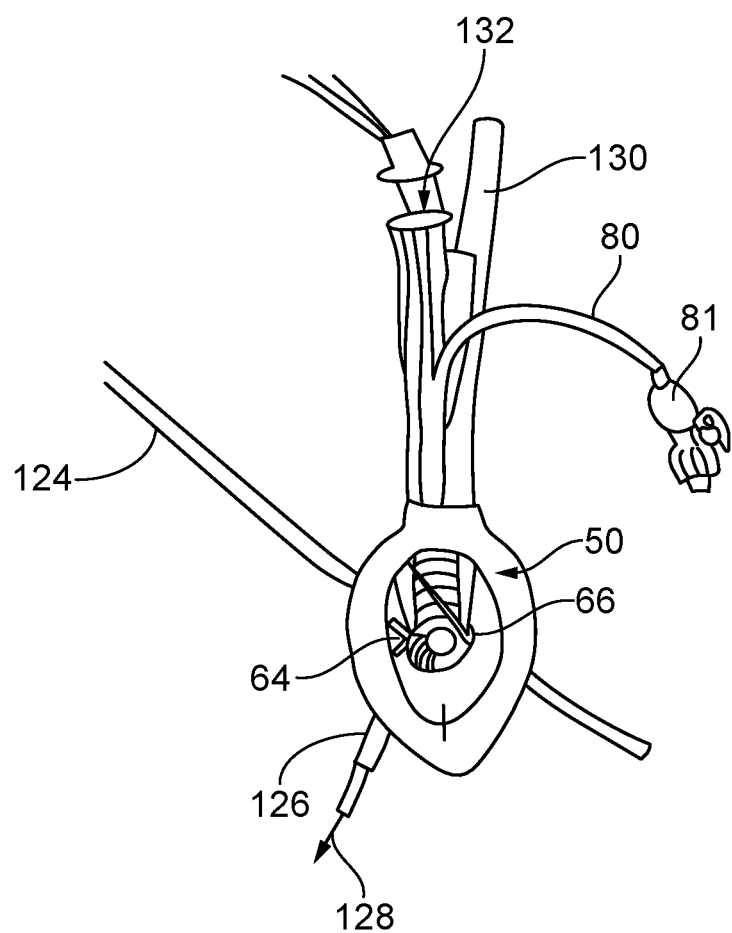
FIG. 15 illustrates the use of the tube exchanger with the present invention.

Referring now to FIG. 15, there is shown use of a tube exchanger 124 with the present invention 50. The tube exchanger 124 is inserted and passes through airway tube 132 of the LMA. The robot head 58 with instruments 64 and 66 are included for medical procedures surrounded by the inflatable cuff of LMA of the present invention 50. The robot head 58 is received into the LMA after passing through the channel 130 for the robot. The inflation line 80 connected to the cuff piece 52 is also shown, along with valve 81. The tube exchanger 124, after passing through the airway channel 132 can be used to reach the trachea and ventilate the trachea of the patient during procedures. This is indicated by flow arrow 128 at the end 126 of tube exchanger 124.

A hollow catheter, such as Cook® hollow catheter, is used for tube exchange and securing the airway. Various commercially available brands may include Cook® Arndt, Aintree, and Frova. The Cook® catheter has a Portex® connector for anesthesia connection and ventilation. In one process, the robotic instrument channel is used to spray the trachea cords of the patient. Room air (at 20%) ventilation to avoid cautery and laser fires. Further, a two-channel endobronchial endotracheal tube can be used with an on/off ventilation window.

Some particular accessories useful with the embodiments described herein for the present invention include: airway exchange catheters, the Cook® retrograde intubation set; the Cook® Soft-tipped Extra Firm Exchange Catheter (for double lumen endotracheal tubes), all of which are available from Cook® Medical; and also jet vent catheter double lumen (such as laser jet 40 cm length 12 CH).

A number of implementations have been described. Nevertheless, it will be understood that various modifications may be made without departing from the spirit and scope of the invention.

In addition, the processes depicted in the figures do not require the particular order shown, or sequential order, to achieve desirable results. In addition, other steps may be provided, or steps may be eliminated, from the described processes, and other components may be added to, or removed from, the described systems. Accordingly, other implementations are within the scope of the following claims.

Elements of different implementations described herein may be combined to form other implementations not specifically set forth above. Elements may be left out of the processes, described herein without adversely affecting their operation. Furthermore, various separate elements may be combined into one or more individual elements to perform the functions described herein.

The invention is not restricted to the details of the foregoing embodiments. The invention extends to any novel one, or any novel combination, of the features disclosed in this specification (including any accompanying claims, abstract and drawings), or to any novel one, or any novel combination, of the steps of any method or process so disclosed.

What is claimed is:
1. A mask for use in robotic surgery comprising:
an airway tube connected to a cuff piece; said cuff piece having an inflatable cuff integrally formed with a back section to said cuff piece;

said inflatable cuff having an inner edge defining a mouth of said inflatable cuff and an inflation line extending from said inflatable cuff;

said back section of said cuff piece having a first channel for receiving a robot head from said airway tube with at least one medical instrument and a second channel for receiving a ventilation tube from said airway tube as said robot head and said ventilation tube are incorporated through said airway tube and extend out from said airway tube to said back section of said cuff piece;

a pliable diaphragm hugging said robot head to seal said mask where said robot head enters said mask;

said robot head and said ventilation tube capable of extending from said mouth of said cuff for medical procedures without an endotracheal tube in place, by controlling a robot connected to said robotic head; and a hollow catheter used for tube exchange and securing an airway, said hollow catheter having a connector for anesthesia connection and ventilation.

2. The mask according to claim 1, wherein said mask is a laryngeal mask airway type mask.

3. The mask according to claim 1, wherein said cuff has a third channel for receiving an anesthesia tube.

4. The mask according to claim 1, further comprising a protective sleeve covering a proximal part of said robot head and sealing said cuff piece of said mask.

5. The mask according to claim 1, wherein said robot head includes a camera and a light.

6. The mask according to claim 1, wherein said ventilation tube is used for anesthesia.

7. The mask according to claim 1, wherein an adaptor is used for ventilation.

8. The mask according to claim 1, wherein a tube exchanger is inserted and passes through said airway tube.

* * * * *